US00PP14057P29

(12) United States Plant Patent
Osiecki

(10) Patent No.: US PP14,057 P2
(45) Date of Patent: Aug. 12, 2003

(54) ANTHURIUM PLANT NAMED 'PICANTE'

(75) Inventor: Marian Wincenty Osiecki, Marianna, FL (US)

(73) Assignee: Oglesby Plants International, Altha, FL (US)

( * ) Notice: Subject to any disclaimer, the term of this patent is extended or adjusted under 35 U.S.C. 154(b) by 0 days.

(21) Appl. No.: 10/119,882

(22) Filed: Apr. 9, 2002

(51) Int. Cl.[7] ..... A01H 5/00
(52) U.S. Cl. ..... Plt./367
(58) Field of Search ..... Plt./367

*Primary Examiner*—Bruce R. Campell
*Assistant Examiner*—Annette H. Para
(74) *Attorney, Agent, or Firm*—C. A. Whealy

(57) ABSTRACT

A distinct cultivar of Anthurium plant named 'Picante', characterized by its upright and outwardly spreading plant habit; freely clumping growth habit; large glossy dark green leaves; red-colored spathes that fade to dark pink in color with development with purple-colored spadices that become green in color with development; inflorescences that are positioned just above and beyond the foliage on strong, straight and thick scapes; freely and continuous flowering habit; good inflorescence longevity; and resistance to *Xanthomonas campestris* pv. dieffenbachia.

2 Drawing Sheets

BOTANICAL CLASSIFICATION/CULTIVAR DESIGNATION

Anthurium hybrid cultivar Picante.

BACKGROUND OF THE INVENTION

The present invention relates to a new and distinct cultivar of Anthurium plant, botanically known as Anthurium hybrid, and hereinafter referred to by the name 'Picante'.

The new cultivar is a product of a planned and controlled breeding program conducted by the Inventor in Altha, Fla. The objective of the breeding program is to develop vigorous pot-type Anthuriums cultivars that are resistant to *Xanthomonas campestris* pv. dieffenbachia and have attractive spathes and foliage.

The new Anthurium originated from a cross-pollination by the Inventor in 1995 of a proprietary Anthurium hybrid seedling selection identified as code number 91-11-48, not patented, as the female or seed parent and a selection of Anthurium hybrid cultivar Lady Jane identified as code number 941, not patented, as the male or pollen parent. The new Anthurium was discovered and selected by the Inventor as a plant within the progeny of the stated cross-pollination in a controlled environment in Altha, Fla., in 1998.

Asexual propagation of the new cultivar by meristem culture in a controlled environment in Altha, Fla., since 1998, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Picante. These characteristics in combination distinguish 'Picante' as a new and distinct cultivar:

1. Upright and outwardly spreading plant habit; symmetrical.
2. Freely clumping growth habit.
3. Large glossy dark green leaves.
4. Red-colored spathes that fade to dark pink in color with development with purple-colored spadices that become green in color with development.
5. Inflorescences that are positioned just above and beyond the foliage on strong, straight and thick scapes.
6. Freely and continuous flowering habit.
7. Good inflorescence longevity.
8. Resistant to *Xanthomonas campestris* pv. dieffenbachia.

Plants of the new Anthurium differ from plants of the female parent, the selection 91-11-48 in the following characteristics:

1. Plants of the new Anthurium are smaller than plants of the selection 91-11-48.
2. Plants of the new Anthurium are more freely clumping and more freely flowering than plants of the selection 91-11-48.
3. Plants of the new Anthurium have smaller, darker green-colored and glossier leaves than plants of the selection 91-11-48.
4. Plants of the new Anthurium have red-colored spathes whereas plants of the selection 91-11-48 have pink-colored spathes.

Plants of the new Anthurium differ from plants of the male parent, the selection of 'Lady Jane' in the following characteristics:

1. Plants of the new Anthurium are more vigorous than plants of the selection of 'Lady Jane'.
2. Plants of the new Anthurium are more freely clumping and more freely flowering than plants of the selection of 'Lady Jane'.
3. Plants of the new Anthurium have darker green-colored and glossier leaves than plants of the selection of 'Lady Jane'.

4. Plants of the new Anthurium have red-colored spathes whereas plants of the selection of 'Lady Jane' have dark pink-colored spathes.

Plants of the new Anthurium can be compared to plants of the cultivar 75-10, disclosed in U.S. Plant Pat. No. 9,355. In side-by-side comparisons conducted in Altha, Fla., plants of the new Anthurium differed from plants of the cultivar 75-10 in the following characteristics:

1. Plants of the new Anthurium had a slightly more open plant habit than plants of the cultivar 75-10.

2. Plants of the new Anthurium had darker green-colored and glossier leaves than plants of the cultivar 75-10.

3. Spathes of plants of the new Anthurium were positioned closer to the foliage than spathes of plants of the cultivar 75-10.

4. Plants of the new Anthurium had thicker scapes than plants of the cultivar 75-10.

5 . Plants of the new Anthurium had narrower spathes than plants of the cultivar 75-10.

6. Spathes of plants of the new Anthurium maintained color and glossiness longer than spathes of plants of the cultivar 75-10.

Plants of the new Anthurium can also be compared to plants of the cultivar A4, disclosed in U.S. Plant Pat. No. 11,728. In side-by-side comparisons conducted in Altha, Fla., plants of the new Anthurium differed from plants of the cultivar A4 in the following characteristics:

1. Plants of the new Anthurium had a slightly more open plant habit than plants of the cultivar A4.

2. Plants of the new Anthurium had narrower, darker green-colored and glossier leaves than plants of the cultivar A4.

3. Plants of the new Anthurium were more freely branching and more freely flowering than plants of the cultivar A4.

4. Plants of the new Anthurium had thinner scapes than plants of the cultivar A4.

5. Plants of the new Anthurium had smaller spathes than plants of the cultivar A4.

6. Spathes of plants of the new Anthurium maintained color and glossiness longer than spathes of plants of the cultivar A4.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs differ slightly from the color values cited in the detailed botanical description which accurately describe the colors of the new Anthurium.

The photograph at the top of the first sheet comprises a side perspective view of a typical flowering plant of the cultivar Picante grown in a container.

The photograph at the bottom of the first sheet comprises a close-up view of a typical flowering plant of the cultivar Picante.

The photograph at the top of the second sheet comprises a close-up view of a typical spathe of the cultivar Picante.

The photograph at the bottom of the second sheet comprises a close-up view of a typical leaf of the cultivar Picante.

DETAILED BOTANICAL DESCRIPTION

The aforementioned photographs and the following observations and measurements describe 18-month old plants grown in 20-cm containers in Altha, Fla., in a polycarbonate-covered greenhouse with day temperatures of 24 to 30° C., night temperatures of 22 to 25° C., and light levels about 800 to 1,500 foot-candles.

In the following description, color references are made to The Royal Horticultural Society Colour Chart, 1995 Edition, except where general terms of ordinary dictionary significance are used.

Botanical classification: Anthurium hybrid cultivar Picante.

Parentage:

*Female, or seed, parent.*—Proprietary Anthurium hybrid seedling selection identified as code number 91-11-48, not patented.

*Male, or pollen, parent.*—Selection of Anthurium hybrid cultivar Lady Jane identified as code number 941, not patented.

Propagation:

*Method.*—By meristem culture.

*Time to initiate roots on a meristem-cultured plant.*—Summer: About 21 to 25 days at soil temperatures of 25 to 30° C. Winter: About 25 to 30 days at soil temperatures of 22 to 27° C.

*Time to produce a rooted young plant.*—Summer: About 91 to 98 days at soil temperatures of 25 to 30° C. Winter: About 105 to 112 days at soil temperatures of 22 to 27° C.

*Root description.*—Strong thick fleshy roots with fine lateral roots.

Plant description:

*Plant shape.*—Upright and outwardly spreading plant habit, inverted triangle, symmetrical.

*Growth habit.*—Freely clumping, about 10 clumps per plant.

*Plant height.*—About 54 cm.

*Plant diameter or spread.*—About 78 cm.

*Foliage description.*—Quantity per plant: About 32. Length: Petiole to apex: About 23 cm. Lobes to apex: About 25 cm. Width: About 15.5 cm. Shape: Cordate. Apex: Sharply acuminate. Base: Cordate; base has two rounded lobes that do not overlap. Margin: Entire. Texture: Leathery; glabrous. Luster: Young leaves, upper and lower surfaces: Glossy. Fully expanded leaves, upper surface: Glossy. Fully expanded leaves, lower surface: Slightly glossy. Venation: Pinnate. Petiole: Length: About 30.5 cm. Diameter: About 5.5 mm. Geniculum: Length: About 3.2 cm. Diameter: About 5.75 mm. Orientation: Curved or bent. Petiole sheath: Length: About 3.8 mm. Width, at midpoint: About 5 mm. Distance from apex of petiole sheath to base of geniculum: About 17.5 cm. Apex: Acute. Cataphyll: New leaves emerge from a cataphyll which turns brown, 200D, with subsequent development and eventually abscises. Length: About 12.5 cm. Width, at base: About 2.1 cm. Shape: Triangular, narrow and tapering. Apex: Apiculate. Margin: Entire. Texture, upper and lower surfaces: Smooth. Color: Young leaves, upper surface: Close to 146A becoming darker than 146A. Young leaves, lower surface: Close to 146A. Fully expanded leaves, upper surface: Darker than 147A. Fully expanded leaves, lower surface: 146A. Venation, upper surface: Close to 146A. Venation, lower surface: 146B to 146D. Petiole: 146A; occasionally overlain with anthocyanin, close to 187A. Geniculum: 144A to 146A. Petiole sheath: 146A; occasionally overlain with anthocyanin, close to 187A. Cataphyll, upper surface: 148C to 148D. Cataphyll, lower surface: 146A.

Inflorescence description:

*Inflorescence arrangement.*—When developing, the spathe is tightly rolled around the spadix and emerges from the petiole sheath. Spathes with spadices held just above and beyond the foliage on straight, strong and thick peduncles. Freely and continuous flowering year-round; about 18 inflorescences in various stages of development per plant at one time.

*Inflorescence longevity.*—Inflorescences maintain good color and substance on the plant for about six to eight weeks. As cut flowers, inflorescences maintain good color and substance for about two to three weeks. Inflorescences persistent.

*Time to flower.*—First flowers develop about nine months after planting rooted plants.

*Spathe.*—Length: About 9.2 cm. Width: About 5.1 cm. Shape: Ovate. Apex: Aristate. Base: Obtuse. Margin: Entire. Texture: Leathery; glabrous. Aspect: Longitudinally concave. Color: Before unrolling, upper and lower surfaces: Close to 53A. Opening and fully opened, front surface: 53B; becoming lighter, 53C to 47A to 48A with subsequent development. Opening and fully opened, back surface: 53C; becoming lighter, 48A to 48C with subsequent development. Eventually front and back surfaces of spathes become green, close to 148A, overlain with close to 48A.

*Spadix.*—Length: About 5.9 cm. Diameter: About 8 mm. Shape: Columnar. Cross section: Rounded. Longitudinal axis: Erect. Color: Immature: 71A to 70A. Mature: 70A; eventually becoming green, 148A, with subsequent development.

*Flowers.*—Quantity per spadix: More than 200. Shape: Roughly triangular. Diameter: About 1 mm or less. Androecium: Anthers and filaments are minute and not clearly visible. Pollen color: Close to 158B. Gynoecium: Pistils are translucent white and protrude between the staminate flowers and just beyond the stamens.

*Scape.*—Length: About 39 cm. Diameter: About 4.25 mm. Strength/aspect: Strong; straight; thick. Color: Towards the spathe, 53A; towards the base, 46A overlain with 187A.

*Pedicel.*—Length: About 3.5 mm. Diameter: About 3 mm. Color: 53A.

*Seed/fruit.*—Seed nor fruit development on plants of the new Anthurium has not been observed.

Disease/pest resistance: In greenhouse tests, plants of the new Anthurium have demonstrated a high degree of resistance to *Xanthomonas campestris* pv. dieffenbachia. Plants of the new Anthurium have not been observed to be resistant to pests common to Anthuriums.

Temperature tolerance: Plants of the new Anthurium have been observed to be tolerant to temperatures ranging from 10 to 40° C.

It is claimed:

1. A new and distinct cultivar of Anthurium plant named 'Picante', as illustrated and described.

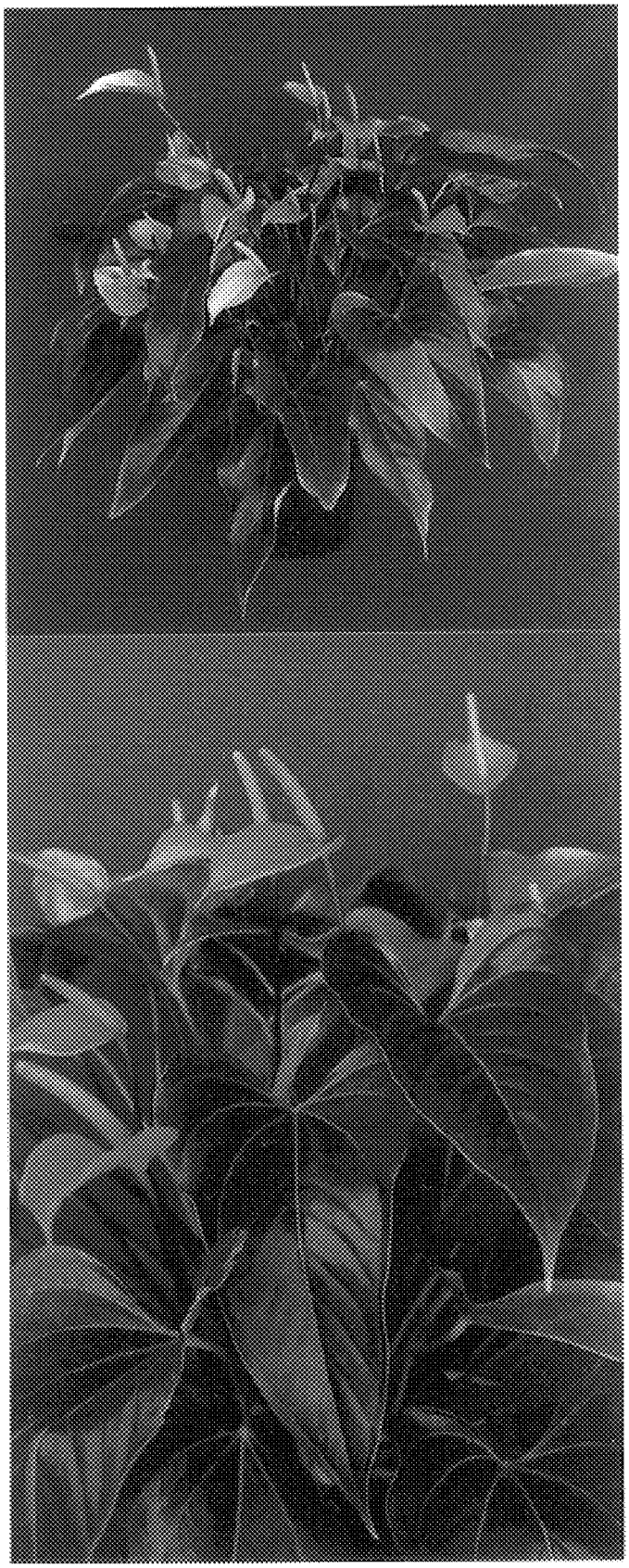

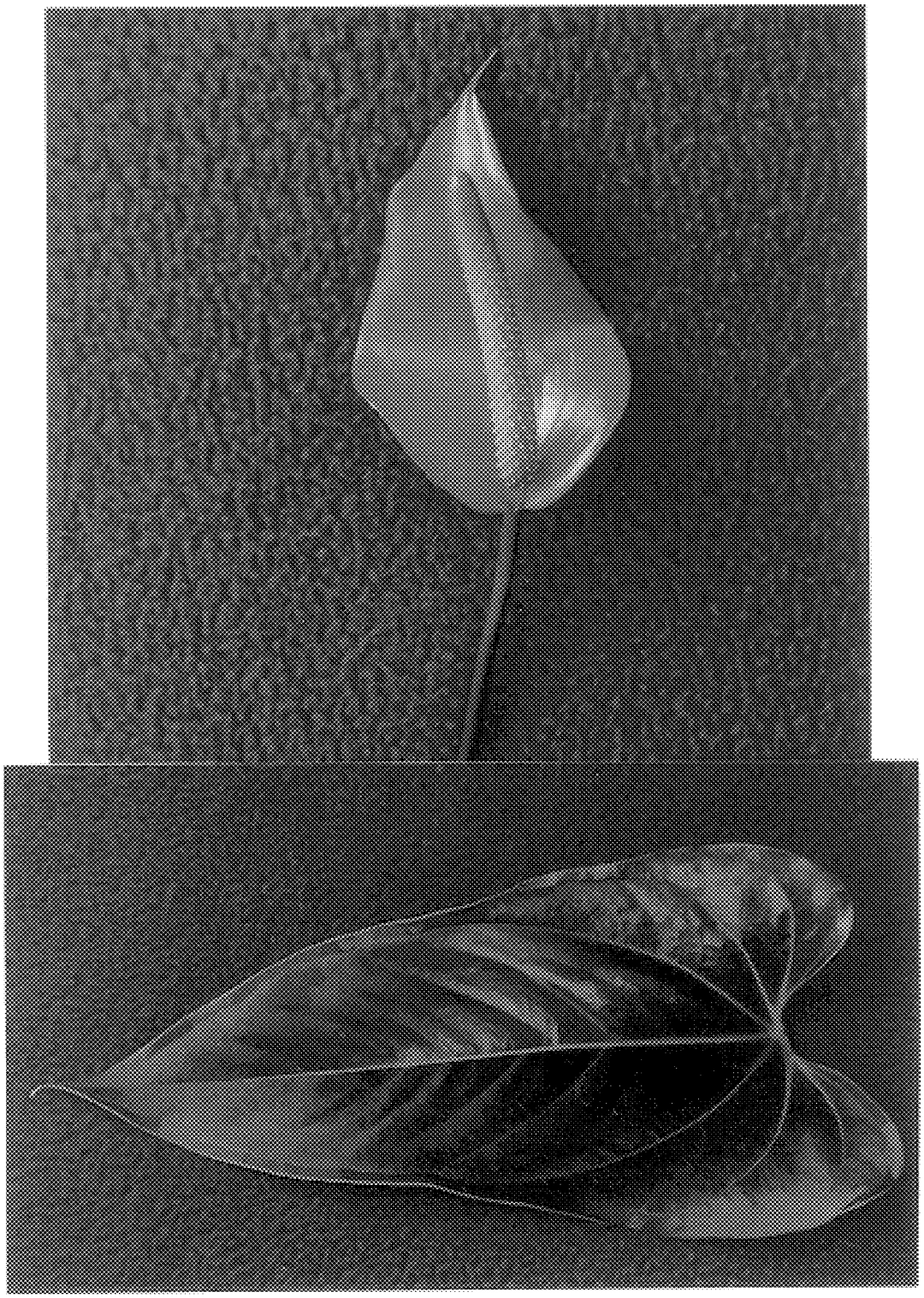

* * * * *